(12) United States Patent
Ono et al.

(10) Patent No.: US 7,879,315 B2
(45) Date of Patent: Feb. 1, 2011

(54) AGENT FOR DISSOLVING DENTAL CALCULI AND DENTAL CARIES

(75) Inventors: Kazuhiro Ono, Saitama (JP); Yuuki Nagata, Kanagawa (JP); Yoshiko Ishii, Kanagawa (JP)

(73) Assignee: Showa Yakuhin Kako Co., Ltd., Tokyo (JP)

( * ) Notice: Subject to any disclaimer, the term of this patent is extended or adjusted under 35 U.S.C. 154(b) by 0 days.

(21) Appl. No.: 10/535,336

(22) PCT Filed: Nov. 19, 2003

(86) PCT No.: PCT/JP03/14709

§ 371 (c)(1),
(2), (4) Date: Jan. 6, 2006

(87) PCT Pub. No.: WO2004/045594

PCT Pub. Date: Jun. 3, 2004

(65) Prior Publication Data

US 2006/0147392 A1 Jul. 6, 2006

(30) Foreign Application Priority Data

Nov. 19, 2002 (JP) ............................... 2002-334984
Oct. 6, 2003 (JP) ............................... 2003-346513

(51) Int. Cl.
| | |
|---|---|
| A61Q 11/00 | (2006.01) |
| A61K 6/00 | (2006.01) |
| A61K 8/00 | (2006.01) |
| A61K 8/36 | (2006.01) |
| A61K 8/97 | (2006.01) |
| A61K 31/00 | (2006.01) |
| A61K 31/01 | (2006.01) |
| A61K 31/015 | (2006.01) |

(52) U.S. Cl. ............................ 424/49; 424/55; 424/58; 514/1; 514/762; 514/763

(58) Field of Classification Search ............. 424/49, 424/58
See application file for complete search history.

(56) References Cited

U.S. PATENT DOCUMENTS

| | | | | |
|---|---|---|---|---|
| 4,130,638 A | * | 12/1978 | Dhabhar et al. | ............... 424/55 |
| 4,335,102 A | * | 6/1982 | Nakashima et al. | ........... 424/52 |
| 4,355,022 A | | 10/1982 | Rabussay | |
| 4,606,912 A | * | 8/1986 | Rudy et al. | ................... 424/52 |
| 4,645,662 A | * | 2/1987 | Nakashima et al. | ........... 424/52 |
| 5,300,289 A | * | 4/1994 | Garlich et al. | ................. 424/54 |
| 5,646,178 A | * | 7/1997 | Walker et al. | ............... 514/456 |
| 5,980,869 A | * | 11/1999 | Sanker et al. | ................. 424/58 |
| 6,436,429 B1 | | 8/2002 | Peyman | |
| 6,726,922 B1 | | 4/2004 | Peyman | |
| 2002/0156130 A1 | * | 10/2002 | Melman | ...................... 514/557 |
| 2005/0100514 A1 | | 5/2005 | Sakaguchi et al. | |

FOREIGN PATENT DOCUMENTS

| | | | |
|---|---|---|---|
| CA | 2328041 | | 6/2002 |
| EP | 0427175 | | 5/1991 |
| JP | 46/7500 | | 5/1970 |
| JP | 56/18911 A | | 2/1981 |
| JP | 06/56687 A | | 3/1994 |
| JP | 8/504816 | | 5/1996 |
| JP | 8/245353 | | 9/1996 |
| JP | 9-110687 | | 4/1997 |
| JP | 9-295942 | | 11/1997 |
| JP | 409295944 | * | 11/1997 |
| JP | 7-053653 | | 12/1997 |
| JP | 2728306 | | 12/1997 |
| JP | 10-017447 | | 1/1998 |
| JP | 2000/63890 A | | 2/2000 |
| JP | 2000-239136 | * | 9/2000 |
| JP | 2001/288062 A | | 10/2001 |
| JP | 2002-020255 | | 1/2002 |
| JP | 2002-047196 | | 2/2002 |
| JP | 2002/540134 | | 11/2002 |
| WO | 89/05135 | | 6/1989 |
| WO | 93/11740 | | 6/1993 |
| WO | 94/14406 | | 7/1994 |
| WO | 0057849 | | 10/2000 |
| WO | 01/17494 | | 3/2001 |
| WO | 01/72144 | | 10/2001 |

OTHER PUBLICATIONS

English Language Abstract of JP 2002-020255.
English Language Abstract of JP 9-110687.
English Language Abstract of JP 9-295942.
English Language Abstract of JP 2002-047196.

(Continued)

*Primary Examiner*—Frederick Krass
*Assistant Examiner*—Lezah W Roberts
(74) *Attorney, Agent, or Firm*—Greenblum & Bernstein, P.L.C.

(57) ABSTRACT

An agent for dissolving dental calculus and/or dental caries, which comprises one or more kinds of substances selected from the group consisting of inositol phosphoric acid esters (e.g., phytic acid), polyphenols (e.g., *Perilla frutescen* var. *crispa* polyphenols), phosphoric acids, edetic acid salts, tartaric acid, malic acid, citric acid, and glycolic acid as an active ingredient. Dental calculus and/or dental caries can be conveniently dissolved in a short period of time.

6 Claims, 1 Drawing Sheet

OTHER PUBLICATIONS

English Language Abstract of JP 10-017447.
English Language Abstract of JP 62-292714.
Nordbo et al., "Desorption of Salivary Proteins from Hydroxyapatite by Phytic Acid and Glycerophosphate and the Plaque-Inhibiting Effect of the Two Compounds In Vivo," Journal of Dental Research, vol. 51, No. 3, pp. 800-811 (1972).
Shinada et al., Koku Eisei Kaishi (Journal of Dental Health), vol. 53, No. 4, Subject No. 03-IE0920 (2003).
English language Abstract of CN 1 105 558 (LUO), (provided by WPI/Thompson, XP-002411277).
English language Abstract of JP2000-63890A.
English language Abstract of JP2001-288062A.
English language Abstract of JP56-18911A.
English language Abstract of JP06-56687A.
English language Abstract of JP2000-63890A, Feb. 2000.
English language Abstract of JP2001-288062A, Oct. 2001.
English language Abstract of JP56-18911A, Feb. 1981.
English language Abstract of JP06-56687A, Mar. 1994.
English language Abstract of CN 1 102 978 (Yao), (provided by WPI/Thompson, XP-002411281), May 1995.
English language Abstract of JP 05-097640 (Ogawa), (provided by WPI/Thompson, XP-002411282), Apr. 1993.
English language Abstract of JP 2002-220332 (Miyoshi), (provided by WPI/Thompson, XP-002411283), Aug. 2002.
English language Abstract of CN 1 105 558 (Luo), (provided by WPI/Thompson, XP-002411277), Mar. 1994.

* cited by examiner

Before the test

After the test

AGENT FOR DISSOLVING DENTAL CALCULI AND DENTAL CARIES

TECHNICAL FIELD

The present invention relates to an agent for dissolving dental calculus and/or dental caries.

BACKGROUND ART

Dental calculus is an ash gray, yellowish or dark brown calcified substance depositing on dental crowns, exposed dental root surfaces, or surfaces of restorative dental materials. Plaque (dental plaque) adheres to surfaces of human teeth. In the plaque, a reaction occurs by which inorganic salts become more adhesive, and calcification starts from a layer which touches a tooth surface. The calcification advances as the plaque becomes older and thicker, and new plaques adhere to the surface of the calcified plaques and causes calcification. Dental calculus is formed by repetition of this process.

Seventy to eighty percents of components of supragingival dental calculus consist of inorganic salts, and most of them consist of hydroxyapatite ($Ca_{10}(PO_4)_6(OH)_2$). Calcium phosphate, calcium carbonate, magnesium phosphate and the like may sometimes be also contained. Further, dibasic calcium phosphate and tribasic calcium phosphate may sometimes be contained. Organic components contained in dental calculus are bacterial cells, and they include cell walls of gram positive bacteria and endotoxins as outer membrane components of gram negative bacteria. Dental plaque formation more easily progresses on dental calculus surfaces than on smooth tooth surfaces, and dental plaque adhering to dental calculus stimulates periodontal soft tissues to become etiologic substance. Accordingly, scaling of teeth is important as one of the fundamental treatments in prophylaxis and therapy of periodontal diseases.

For removal of dental calculus, methods involving mechanical removal of calculus by using a scaler or the like have been conventionally applied. However, the methods have problems in that the treatment takes a long period of time due to hardness of dental calculus, and thus patients, dentists, or dental hygienists bear burdens. As a means for chemically dissolving and removing dental calculus, for example, an agent for dissolving dental calculus described in Japanese Patent Publication (KOKOKU) No. 7-53653 is known. However, the dissolution action of the agent is totally insufficient from a practical view, and due to irritancy by chemicals on periodontal soft tissues, the agent has not been used in the field of clinical dentistry. Under the circumstances, it is desired to develop an agent for dissolving dental calculus that can dissolve dental calculus in a short period of time and dose not irritate or damage tissues in oral cavity such as periodontal soft tissues or dental tissues. It has been reported that phytic acid is effective for suppressing dental plaque formation (Nordbo H., et al., J. Dent. Res., 51, 800, 1972). However, this reference neither suggests nor teaches that phytic acid has an action of dissolving dental calculus.

When a dental caries is formed, a therapy generally applied involves cutting and shaving off the caries by using a rotary cutting instrument. However, the therapy has a problem in that a patient is scared by vibration and sound of the instrument, generation of pain and the like during the treatment. When a dental caries is soft, the caries may be scraped by using a dental instrument called an excavator. However, it is difficult to completely scrape a dental caries. Recently, a method has been used which includes dissolving dental caries by using an agent for dissolving dental caries developed in Sweden and then scraping off the caries by using a unique instrument (trade name: Carisolv, produced by Medi Team, Japanese Patent No. 2728306). However, this method has a problem in that softening effect of Carisolv is weak and thus the treatment takes a long period of time. Furthermore, the method also has drawbacks in that the treatment requires a mixing step before use, which is a complicated operation, and that the agent has poor storage stability and the like. For these reasons, it is desired to provide an agent for dissolving dental caries that can easily dissolve and soften dental caries and has superior storage stability, and achieves a treatment with convenient operations.

DISCLOSURE OF THE INVENTION

An object of the present invention is to provide an agent for dissolving dental calculus and/or dental caries that can conveniently dissolve dental calculus and/or dental caries in a short period of time. Further, another object of the present invention is to provide an agent for dissolving dental calculus and/or dental caries that has the aforementioned characteristics, and dose not irritate or damage tissues in oral cavity such as periodontal soft tissues or dental tissues and has superior storage stability.

The inventors of the present invention conducted various researches to achieve the aforementioned objects, and as a result, they found that one or more kinds of substances selected from the group consisting of inositol phosphoric acid esters, polyphenols, phosphoric acids, edetic acid salts, tartaric acid, malic acid, citric acid, and glycolic acid have superior properties as an agent for dissolving dental calculus and/or dental caries. The present invention was achieved on the basis of the above findings.

The present invention thus provides an agent for dissolving dental calculus and/or dental caries, which comprises one or more kinds of substances selected from the group consisting of inositol phosphoric acid esters, polyphenols, phosphoric acids, edetic acid salts, tartaric acid, malic acid, citric acid, and glycolic acid as an active ingredient.

According to preferred embodiments of the present invention, there are provided the aforementioned agent for dissolving dental calculus and/or dental caries, which contains phytic acid as an active ingredient; the aforementioned agent for dissolving dental calculus and/or dental caries, which contains one or more kinds of substances selected from the group consisting of *Perilla frutescen* var. *crispa* polyphenols, cassis polyphenols, hop polyphenols, sugar cane polyphenols, and disodium edetate as an active ingredient; the aforementioned agent for dissolving dental calculus and/or dental caries, which further contains an inorganic metal salt; the aforementioned agent for dissolving dental calculus and/or dental caries, wherein the inorganic metal salt is sodium chloride; the aforementioned agent for dissolving dental calculus and/or dental caries, which further contains a bacteriolytic enzyme; the aforementioned agent for dissolving dental calculus and/or dental caries, wherein the bacteriolytic enzyme consists of one or more kinds of bacteriolytic enzymes selected from the group consisting of albumen lysozyme, pectinases, proteases, and alginate lyases; the aforementioned agent for dissolving dental calculus and/or dental caries, which further contains a surface active agent; the aforementioned agent for dissolving dental calculus and/or dental caries, wherein the surface active agent is cetrimide; and the aforementioned agent for dissolving dental calculus and/or dental caries, which is used for a human or a mammal other than a human.

From another aspect, the present invention provides a method for dissolving dental calculus and/or dental caries, which comprises the step of bringing one or more kinds of substances selected from the group consisting of inositol phosphoric acid esters, polyphenols, phosphoric acids, edetic acid salts, tartaric acid, malic acid, citric acid, and glycolic acid into contact with the dental calculus and/or dental caries. According to a preferred embodiment of the aforementioned method, the method comprising the step of applying a solution containing the aforementioned substances to the dental calculus and/or dental caries is provided. Furthermore, from a further aspect, the present invention provides use of one or more kinds of substances selected from the group consisting of inositol phosphoric acid esters, polyphenols, phosphoric acids, edetic acid salts, tartaric acid, malic acid, citric acid, and glycolic acid for manufacture of the aforementioned agent for dissolving dental calculus and/or dental caries.

BEST MODE FOR CARRYING OUT THE INVENTION

Figure 1:
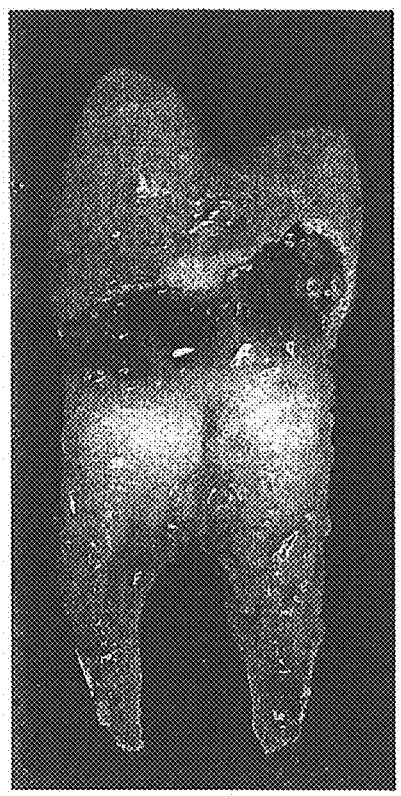
FIG. 1 shows the effect of the agent for dissolving dental caries of the present invention. In the figure, "Before the test" indicates the tooth before the treatment with the agent for dissolving dental caries, and "After the test" indicates the tooth after the treatment with the agent for dissolving dental caries, of which dental caries was removed by using an excavator after the treatment (right side of the tooth).
Figure 1:

As the active ingredient of the agent for dissolving dental calculus and/or dental caries of the present invention, one or more kinds of substances selected from the group consisting of inositol phosphoric acid esters, polyphenols, phosphoric acids, edetic acid salts, tartaric acid, malic acid, citric acid, and glycolic acid can be used. Preferably, one or more kinds of substances selected from the group consisting of inositol phosphoric acid esters, polyphenols, and edetic acid salts can be used.

Although the stereochemistry of the inositol phosphoric acid esters is not particularly limited, preferred are, for example, meso-inositol (also called myoinositol, dambose or phaseomannite), D-inositol, L-inositol, DL-inositol, scyllit and the like. Although the number of phosphate portions of the inositol phosphoric acid esters is not particularly limited, hexaphosphoric acid esters are preferred. Among the hexaphosphoric acid esters, meso-inositol hexaphosphoric acid ester (phytic acid) is preferred. As the active ingredient of the agent for dissolving dental calculus of the present invention, two or more kinds of inositol phosphoric acid esters may be used in combination.

The inositol phosphoric acid esters can be easily obtained by those skilled in the art. For example, phytic acid is a substance contained in seeds and cereals, especially rice bran, and has been used in the field of foodstuffs and medical filed, and easily obtained as a commercial product. For example, products containing 48 to 52% of phytic acid are sold as foodstuff improvers by Daiichi Pharmaceutical Co., Ltd. or Tsuno Food Industrial Co., Ltd., and therefore these products may be used as the agent for dissolving dental calculus of the present invention without any treatment, or after suitable dilution with water, buffer or the like.

The types of the polyphenols are not particularly limited. For example, *Perilla frutescen* var. *crispa* polyphenols, cassis polyphenols, tea polyphenols, buckwheat polyphenols, cranberry polyphenols, grape seed polyphenols, Rubini polyphenols, sugar cane polyphenols, hop polyphenols and the like can be used. Among them, *Perilla frutescen* var. *crispa* polyphenols rich in rosemarinic acid and cassis polyphenol rich in anthocyanins are preferred. Polyphenols can be easily obtained by those skilled in the art. For example, *Perilla frutescen* var. *crispa* polyphenols are substances contained in *Perillia frutescen* var. *crispa*, and cassis polyphenols are substances contained in cassis, which are used as preferred substances for health maintenance in the field of foodstuffs, and can be easily obtained as commercial products. For example, *Perilla frutescen* var. *crispa* polyphenols are sold as a food improver from Meiji Seika Kaisha, Ltd. Purified or roughly purified polyphenols may be used as the polyphenols, or natural products and natural extracts rich in polyphenols can also be used without any treatment. For example, purple potato color containing polyphenols and the like may be used. It has been elucidated that polyphenols have superior functions of removing active oxygen in vivo, improving blood flows, giving relaxation effect, and the like. It has been confirmed that anthocyanins contained in cassis polyphenols have effects of improving blood flows of capillary vessels and increasing the regeneration rate of rhodopsin, which is a photoreceptor substance in the retina, to reduce the photesthesia threshold value. As for hop polyphenols, dental plaque adhesion suppressing effect has been reported (Shinada et al., Koku Eisei Kaishi (Journal of Dental Health), 53 (4), Subject No. 03-1E0920, 2003). However, it has not been reported so far that polyphenols can dissolve dental calculus and/or dental caries.

Edetic acid salts can be easily obtained by those skilled in the art. As the edetic acid salts, for example, disodium edetate, trisodium edetate, tetrasodium edetate and the like can be used. Among them, disodium edetate is preferred. Disodium edetate, for example, is a so-called chelating agent that binds a metal ion of heavy metal compound in the molecule to form a stable cyclic compound and deactivate the compound, and is conventionally used as an antidote for heavy metals poisoning. In the field of foodstuffs, the substance may be used for purposes of antidiscoloration and antioxidation on the basis of the aforementioned property. However, it has not been reported so far that edetic acid salts can dissolve dental calculus and/or dental caries. As phosphoric acids, phosphoric acid, polyphosphoric acid, pyrophosphoric acid and the like can be used, and phosphoric acid is preferred.

The agent for dissolving dental calculus or dental caries of the present invention can be used generally in the form of a solution. For example, an aqueous solution containing one or more kinds of substances selected from the group consisting of inositol phosphoric acid esters, polyphenols, phosphoric acids, edetic acid salts, tartaric acid, malic acid, citric acid, and glycolic acid, preferably one or more kinds of substances selected from the group consisting of phytic acid, *Perilla frutescen* var. *crispa* polyphenols, cassis polyphenols, and disodium edetate, at a ratio of about 5 to 40% by weight can be prepared and applied to dental calculus or dental caries. When phosphoric acid is used as the active ingredient of the agent for dissolving dental calculus and/or dental caries of the present invention, a concentration of phosphoric acid is preferably 30% by weight or less, more preferably 15% by weight or less, most preferably about 10% by weight, based on the total weight of the composition. When tartaric acid, malic acid, citric acid, or glycolic acid is used as the active ingredient of the agent for dissolving dental calculus and/or dental caries of the present invention, the concentration of these substances is preferably 30% by weight or less, more preferably 15% by weight or less, most preferably about 10% by weight, based on the total weight of the composition. When the agent for dissolving dental calculus or dental caries of the present invention is prepared as an aqueous solution, a small amount of an organic solvent miscible with water may be added. Examples of the organic solvent include, for example, ethanol, glycerin, ethylene glycol and the like.

The agent for dissolving dental calculus and/or dental caries of the present invention may be added with an inorganic metal salt, preferably one or more kinds of inorganic metal salts selected from the group consisting of alkali metal salts and alkaline earth metal salts. As the inorganic metal salt, sodium chloride is preferred. An amount of the inorganic metal salt added is not particularly limited. For example, the amount may be about 10 to 50% by weight, based on the weight of the substance selected from the group consisting of inositol phosphoric acid esters, polyphenols, phosphoric acids, edetic acid salts, tartaric acid, malic acid, citric acid, and glycolic acid (when two or more kinds of substances are contained, the weight percent is for their total weight). However, the amount of the inorganic metal salt may be suitably increased or decreased.

A bacteriolytic enzyme and/or a surface active agent may be added to the agent for dissolving dental calculus and/or dental caries of the present invention. As the bacteriolytic enzyme, for example, albumen lysozyme, pectinases (for example, "Pectinase Nagase", Nagase ChemteX Corporation and the like), proteases (for example, "Bioprase conc.", Nagase ChemteX Corporation and the like), alginate lyases (for example, "Alginate Lyase S", Nagase ChemteX Corporation and the like), and the like may be used. Albumen lysozyme is an enzyme having an action of lysing cell membranes of bacteria and exists in eggs of hen. The enzyme is a basic protein rich in arginine, aspartic acid, and tryptophan as being a feature of amino acid composition. As the surface active agent, for example, cetrimide and the like can be used. Cetrimide is a surface active agent mainly consisting of myristyltrimethylammonium bromide, which is a quaternary ammonium salt, and the substance has been generally used as a fungicide and disinfecting agent and added to some disinfectants.

The agent for dissolving dental calculus and/or dental caries of the present invention can also be used as a semi-solid having a gel or thixotropic property by addition with an appropriate pharmaceutical additive such as a gelling agent. The agent can also be prepared in the form of an ointment, or the agent may be blended in toothbrushing agents or solutions for washing of the oral cavity used before toothbrushing (for example, dental rinse or mouthwash). The agent for dissolving dental calculus and/or dental caries of the present invention can also be added with one or more kinds of pH modifiers, buffering substances, preservatives, osmoregulating agents, thickners, dyes and the like, which are generally used as pharmaceutical additives. Furthermore, the agent for dissolving dental calculus and/or dental caries of the present invention may also added with active zeolite, iron oxide, quicklime or the like and used as a thermal dissolving agent. It is also preferable to blend the agent for dissolving dental calculus and/or dental caries of the present invention in a toothbrushing agent provided as a thermal toothbrushing agent (for example, toothbrushing agents of the "Check Periodontal Care Series", Kao Corp., blended with active zeolite, and the like).

For example, when the agent for dissolving dental calculus and/or dental caries of the present invention is prepared as a toothbrushing agent, ingredients ordinarily used for toothbrushing agents can be used such as, for example, basal ingredients including calcium hydrogenphosphate, aluminum hydroxide, calcium carbonate, glycerin, sorbit, sodium laurylate, carboxymethylcellulose sodium, sodium arginate, carragheenan, saccharin sodium, menthol, and mints, and medicinal ingredients including sodium monofluorophosphate, sodium fluoride, cetylpyridinium chloride, tranexamic acid, dipotassium glycyrrhizinate, β-glycyrrhetic acid, chlorhexidine hydrochloride, dl-α-tocopherol acetate, sodium chloride, triclosan, dextrase, sodium polyphosphate, aluminum lactate, potassium nitrate, and polyethylene glycol. However, the ingredients are not limited to these examples. When the agent for dissolving dental calculus and/or dental caries of the present invention is prepared as a dental rinse, ingredients ordinarily used for manufacture of dental rinse can be used such as, for example, ethanol, thymol, 1,8-cineole, methyl salicylate, 1-menthol, benzoic acid, polyoxyethylene polyoxypropylene glycol, and sodium benzoate. However, the ingredients are not limited to these examples.

Methods for using the agent for dissolving dental calculus and/or dental caries of the present invention are not particularly limited. When the agent is prepared as a preparation in the form of a solution, the dissolving agent may be impregnated in absorbent cotton or swab and applied to dental calculus or dental caries by using an appropriate instrument such as a pair of tweezers as required. After the application, a part or whole of dental calculus is dissolved within several minutes and the calculus comes to be easily separated from the tooth surface. A part or whole of the dental caries is also dissolved within several minutes and the caries comes to be successfully scraped completely. After the application, the applied portion may be warmed with visible light, laser light or the like used for starting polymerization of dental resin. Moreover, the preparation may be warmed in advance by using an instrument for warming a mosquito mat and liquid or the like and then applied. By the warming, the dissolution reaction can be promoted.

The term "dissolution of dental calculus and/or dental caries" and synonyms thereof used in the specification should be construed in the broadest sense including a phenomenon that dental calculus and/or dental caries is softened by microscopic dissolution of the dental calculus and/or dental caries, in addition to a phenomenon that dental calculus and/or dental caries is macroscopically dissolved, and should not be construed in any limitative way. For example, suppression of dental calculus formation or dental caries formation by dissolution and removal of dental calculus or dental caries portion at an early stage of the formation is also encompassed by the dissolution of dental calculus or dental caries. The agent for dissolving dental calculus and/or dental caries of the present invention can be used for a human and a mammal other than a human. For example, the agent can also be used as a agent for dissolving dental calculus for animals.

EXAMPLES

The present invention will be explained more specifically with reference to the following examples. However, the scope of the present invention is not limited to these examples.

Example 1

Dental calculus in an amount of 3.0 mg obtained by washing dental calculus collected from the oral cavity and then wiping water with KIMWIPES was immersed in 1 ml of an aqueous solution containing 0.5 g of phytic acid (prepared as a 15% aqueous solution by diluting phytic acid having a content of 48 to 52% produced by Daiichi Pharmaceutical Co., Ltd.) for 5 or 10 minutes. After the treatment, each dental calculus was washed with water, wiped with KIMWIPES and weighted. The weight of each calculus was 2.6 mg or 2.1 mg, and thus remarkable reduction of the weight of dental calculus was observed.

Example 2

Dental calculus in an amount of 3.0 mg obtained by washing dental calculus collected from the oral cavity and then wiping water with KIMWIPES was immersed in 1 ml of an aqueous solution containing 0.5 g of phytic acid (prepared as a 15% aqueous solution by diluting phytic acid having a content of 48 to 52% produced by Daiichi Pharmaceutical Co., Ltd.) and 0.1 g of sodium chloride for 5 or 10 minutes. After the treatment, each dental calculus was washed with water, wiped with KIM WIPES and weighted. The weight of each calculus was 2.4 mg or 1.4 mg, and thus far remarkable reduction of the weight of dental calculus was observed as compared with Example 1.

Example 3

Dental calculus in an amount of 0.6 mg obtained by washing dental calculus collected from the oral cavity and then wiping water with KIMWIPES was immersed in 1 ml of an aqueous solution of *Perilla frutescen* var. *crispa* polyphenols (produced by Meiji Seika Kaisha, Ltd., prepared as a 5% aqueous solution) for 105 minutes. After the treatment, the dental calculus was washed with water, wiped with KIMWIPES and weighted. The weight was 0.3 mg, and thus remarkable reduction of the weight of dental calculus was observed.

Example 4

Dental calculus in an amount of 1.0 mg obtained by washing dental calculus collected from the oral cavity and then wiping water with KIMWIPES was immersed in 1 ml of an aqueous solution of cassis polyphenols (produced by Meiji Seika Kaisha, Ltd., prepared as a 20% aqueous solution) for 90 minutes. After the treatment, the dental calculus was washed with water, wiped with KIMWIPES and weighted. The weight was 0.5 mg, and thus remarkable reduction of the weight of dental calculus was observed.

Example 5

Dental calculus in an amount of 1.2 mg obtained by washing dental calculus collected from the oral cavity and then wiping water with KIMWIPES was immersed in 1 ml of an aqueous solution of *Perilla frutescen* var. *crispa* polyphenols (produced by Meiji Seika Kaisha, Ltd.) and phytic acid (produced by Daiichi Pharmaceutical Co., Ltd.) prepared as a 5% and 12.5% solution for respective ingredients for 7 minutes. After the treatment, the dental calculus was washed with water, wiped with KIMWIPES and weighted. The weight was 0.6 mg, and thus remarkable reduction of the weight of dental calculus was observed.

Example 6

Dental calculus in an amount of 1.2 mg obtained by washing dental calculus collected from the oral cavity and then wiping water with KIMWIPES was immersed for 4 minutes and 30 seconds in 1 ml of an aqueous solution of *Perilla frutescen* var. *crispa* polyphenols (produced by Meiji Seika Kaisha, Ltd.), phytic acid (produced by Daiichi Pharmaceutical Co., Ltd.) and sodium chloride prepared as a 5%, 12.5% and 16.6% solution, respectively. After the treatment, the dental calculus was washed with water, wiped with KIMWIPES and weighted. The weight was 0.6 mg, and thus remarkable reduction of the weight of dental calculus was observed.

Example 7

Dental calculus in an amount of 1.2 mg obtained by washing dental calculus collected from the oral cavity and then wiping water with KIMWIPES was immersed for 4 minutes and 30 seconds in 1 ml of an aqueous solution of cassis polyphenols (produced by Meiji Seika Kaisha, Ltd.), phytic acid (produced by Daiichi Pharmaceutical Co., Ltd.) and sodium chloride prepared as a 5%, 12.5% and 16.6% solution, respectively. After the treatment, the dental calculus was washed with water, wiped with KIMWIPES and weighted. The weight was 0.6 mg, and thus remarkable reduction of the weight of dental calculus was observed.

Example 8

Dental calculus in an amount of 0.50 mg obtained by washing dental calculus collected from the oral cavity and then wiping water with KIMWIPES was immersed in 1 ml of an aqueous solution of disodium edetate prepared as a 14.3% solution for 44 minutes. After the treatment, the dental calculus was washed with water, wiped with KIMWIPES and weighted. The weight was 0.25 mg, and thus remarkable reduction of the weight of dental calculus was observed.

Example 9

Dental calculus in an amount of 1.12 mg obtained by washing dental calculus collected from the oral cavity and then wiping water with KIMWIPES was immersed in 1 ml of an aqueous solution of disodium edetate and cetrimide prepared as a 14.3% and 0.084% solution for respective ingredients for 40 minutes. After the treatment, the dental calculus was washed with water, wiped with KIMWIPES and weighted. The weight was 0.56 mg, and thus remarkable reduction of the weight of dental calculus was observed.

Example 10

Dental calculus in an amount of 0.79 mg obtained by washing dental calculus collected from the oral cavity and then wiping water with KIMWIPES was immersed for 40 minutes in 1 ml of an aqueous solution of disodium edetate and albumen lysozyme prepared as a 14.3% and 10% solution, respectively. After the treatment, the dental calculus was washed with water, wiped with KIMWIPES and weighted. The weight was 0.40 mg, and thus remarkable reduction of the weight of dental calculus was observed.

Example 11

Dental calculus in an amount of 1.2 mg obtained by washing dental calculus collected from the oral cavity and then wiping water with KIMWIPES was immersed in 1 ml of a 10% aqueous solution of phosphoric acid for 7 minutes and 30 seconds. After the treatment, the dental calculus was washed with water, wiped with KIMWIPES and weighted. The weight was 0.6 mg, and thus remarkable reduction of the weight of dental calculus was observed.

Example 12

Dental calculus in an amount of 1.4 mg obtained by washing dental calculus collected from the oral cavity and then wiping water with KIMWIPES was immersed in 1 ml of a 2% aqueous solution of phosphoric acid for 8 minutes and 30 seconds. After the treatment, the dental calculus was washed with water, wiped with KIMWIPES and weighted. The weight was 0.7 mg, and thus remarkable reduction of the weight of dental calculus was observed.

Example 13

Dental calculus in an amount of 1.5 mg obtained by washing dental calculus collected from the oral cavity and then wiping water with KIMWIPES was immersed in 1 ml of a 10% aqueous solution of polyphosphoric acid for 7 minutes and 30 seconds. After the treatment, the dental calculus was washed with water, wiped with KIMWIPES and weighted. The weight was 0.7 mg, and thus remarkable reduction of the weight of dental calculus was observed.

Example 14

Dental calculus in an amount of 2.2 mg obtained by washing dental calculus collected from the oral cavity and then wiping water with KIMWIPES was immersed in 1 ml of a 10% aqueous solution of pyrophosphoric acid for 7 minutes. After the treatment, the dental calculus was washed with water, wiped with KIMWIPES and weighted. The weight was 1.1 mg, and thus remarkable reduction of the weight of dental calculus was observed.

Example 15

Dental calculus in an amount of 0.8 mg obtained by washing dental calculus collected from the oral cavity and then wiping water with KIMWIPES was immersed in 1 ml of a 10% aqueous solution of tartaric acid for 5 minutes. After the treatment, the dental calculus was washed with water, wiped with KIMWIPES and weighted. The weight was 0.4 mg, and thus remarkable reduction of the weight of dental calculus was observed.

Example 16

Dental calculus in an amount of 1.3 mg obtained by washing dental calculus collected from the oral cavity and then wiping water with KIMWIPES was immersed in 1 ml of a 10% aqueous solution of citric acid for 13 minutes. After the treatment, the dental calculus was washed with water, wiped with KIMWIPES and weighted. The weight was 0.65 mg, and thus remarkable reduction of the weight of dental calculus was observed.

Example 17

Dental calculus in an amount of 1.2 mg obtained by washing dental calculus collected from the oral cavity and then wiping water with KIMWIPES was immersed in 1 ml of a 10% aqueous solution of malic acid for 13 minutes. After the treatment, the dental calculus was washed with water, wiped with KIMWIPES and weighted. The weight was 0.6 mg, and thus remarkable reduction of the weight of dental calculus was observed.

Example 18

Dental calculus in an amount of 0.9 mg obtained by washing dental calculus collected from the oral cavity and then wiping water with KIMWIPES was immersed in 1 ml of a 10% aqueous solution of glycolic acid for 9 minutes. After the treatment, the dental calculus was washed with water, wiped with KIMWIPES and weighted. The weight was 0.5 mg, and thus remarkable reduction of the weight of dental calculus was observed.

Example 19

Using a tooth that was extracted from the oral cavity and had dental caries, a gel composition prepared by adding water to *Perilla frutescen* var. *crispa* polyphenol (produced by Meiji Seika Kaisha, Ltd.), phytic acid (produced by Daiichi Pharmaceutical Co., Ltd.) and microparticle silica (concentrations were 2%, 12.5% and 10%, respectively) was adhered to the area of the dental caries, and after 5 minutes, the caries was gently scraped by using an excavator (see, FIG. 1, the right side of the tooth indicated as "After the test"). The caries of the left side of the tooth in the photograph was gently removed only by using an excavator, which is indicated as a control (see, FIG. 1). Apparently, the caries of the right side of the tooth was cleanly removed, whereas a hard black portion remained in the left side as the control, which indicates insufficient removal of the caries.

INDUSTRIAL APPLICABILITY

The agent for dissolving dental calculus and/or dental caries of the present invention has an extremely superior dissolving action on dental calculus and/or dental caries, and has a feature that the agent enables a convenient treatment without necessity of preparation by mixing of chemicals and the like. Moreover, the agent does not substantially irritate or damage tissues in oral cavity such as periodontal soft tissues or dental tissues, and has superior stability. Accordingly, the agent can be suitably used as a safe agent for dissolving dental calculus and/or dental caries in the field of dentistry.

What is claimed is:

1. An agent for dissolving dental calculus, which comprises a composition comprising 10% to 30% by weight glycolic acid and 5% to 40% by weight of an aqueous extract from *Perillafrutescens* var. *crispa flutescen purpurea* comprising rosmarinic acid, the aqueous extract and the glycolic acid being present as a combination of active ingredients in an amount effective to achieve dissolving of dental calculus.

2. The agent for dissolving dental calculus according to claim 1, further comprising cassis polyphenols, hop polyphenols, or sugar cane polyphenols.

3. The agent for dissolving dental calculus according to claim 1, which further comprises an inorganic metal salt.

4. The agent for dissolving dental calculus according to claim 3, wherein the inorganic metal salt is sodium chloride.

5. The agent for dissolving dental calculus according to claim 1, which further comprises a bacteriolytic enzyme.

6. The agent for dissolving dental calculus according to claim 5, wherein the bacteriolytic enzyme is selected from the group consisting of albumen lysozyme, pectinases, proteases, and alginate lyases.

* * * * *

UNITED STATES PATENT AND TRADEMARK OFFICE
CERTIFICATE OF CORRECTION

| | | |
|---|---|---|
| PATENT NO. | : 7,879,315 B2 | Page 1 of 1 |
| APPLICATION NO. | : 10/535336 | |
| DATED | : February 1, 2011 | |
| INVENTOR(S) | : K. Ono et al. | |

It is certified that error appears in the above-identified patent and that said Letters Patent is hereby corrected as shown below:

Title Page;

On Cover Page, Abstract (57) of the printed patent, at line 4, please change "*frutescen*" to --*frutescens*--.

On the Cover Page, Abstract, (57) of the printed patent, at line 5, insert --*flutescen purpurea*-- after *crispa*.

At Column 10, line 44, (claim 1, line 4), of the printed patent, "Perillafrutescens" should be --Perilla frutescens--.

Signed and Sealed this
Thirtieth Day of August, 2011

David J. Kappos
*Director of the United States Patent and Trademark Office*